(12) United States Patent
Boehmdoerfer (10) Patent No.: US 10,238,410 B2
(45) Date of Patent: Mar. 26, 2019

(54) MEDICAL INSTRUMENT

(71) Applicant: S & T AG, Neuhausen am Rheinfall (CH)

(72) Inventor: Richard Boehmdoerfer, Jestetten (DE)

(73) Assignee: S&T AG, Neuhausen am Rheinfall (CH)

( * ) Notice: Subject to any disclaimer, the term of this patent is extended or adjusted under 35 U.S.C. 154(b) by 71 days.

(21) Appl. No.: 15/121,168

(22) PCT Filed: Feb. 2, 2015

(86) PCT No.: PCT/EP2015/052091
§ 371 (c)(1),
(2) Date: Aug. 24, 2016

(87) PCT Pub. No.: WO2015/124416
PCT Pub. Date: Aug. 27, 2015

(65) Prior Publication Data
US 2017/0007286 A1    Jan. 12, 2017

(30) Foreign Application Priority Data

Feb. 24, 2014 (EP) .................................... 14156385

(51) Int. Cl.
*A61B 17/30* (2006.01)
*A61B 17/00* (2006.01)

(52) U.S. Cl.
CPC .... *A61B 17/30* (2013.01); *A61B 2017/00429* (2013.01); *A61B 2017/00433* (2013.01)

(58) Field of Classification Search
CPC .......... A61B 5/150259; A61B 17/2841; A61B 17/50; A61B 2017/505;
(Continued)

(56) References Cited

U.S. PATENT DOCUMENTS

| 4,800,880 A | 1/1989 | Catalano |
| 4,928,962 A | 5/1990 | Finley |

(Continued)

FOREIGN PATENT DOCUMENTS

| DE | 102007047059 | 4/2009 | |
| DE | 102007047059 A1 * | 4/2009 | ............. A61B 17/00 |

(Continued)

OTHER PUBLICATIONS

International search report for Apln. No. PCT/EP2015/052091 dated Mar. 17, 2015.
(Continued)

*Primary Examiner* — Shaun David
*Assistant Examiner* — Brigid K Byrd
(74) *Attorney, Agent, or Firm* — Bachman & LaPointe, PC (57) ABSTRACT

A medical instrument, in particular a surgical instrument, with an intervention portion (20) for a medical intervention, and with a grip (14) designed for holding the instrument, preferably for actuating the intervention portion, with a grip surface portion (1) which is made of a stainless metal and which has an arrangement with shapings (0) and, formed between the shapings, enclosure portions (4, 5, 6, 7), characterized in that the shapings (0) each have a hexagonal edge (2) with six edge portions of equal length (3-1, 3-2, 3-3, 3-4, 3-5, 3-6), wherein mutually adjoining edge portions (3-1, 3-2; 3-2, 3-3; ...) of each shaping (0) upstream and/or downstream of a winding of the arrangement on a plane surface span the same angle ($\varphi$) of 120 degrees, and wherein the edge (2) is formed by the enclosure portions (4, 5, 6, 7) formed between adjacent shapings (0), as a result of which a honeycomb structure (9) is obtained.

19 Claims, 4 Drawing Sheets

(58) Field of Classification Search
CPC ............. A61B 2017/0042–2017/00424; A61B 2017/00429–2017/00433; A61B 17/30
See application file for complete search history.

(56) References Cited

U.S. PATENT DOCUMENTS

| | | | | | |
|---|---|---|---|---|---|
| 4,973,300 | A * | 11/1990 | Wright | ................... | A61B 17/02 600/37 |
| 4,991,842 | A * | 2/1991 | Finley | ................... | A63B 41/08 40/327 |
| 5,047,049 | A * | 9/1991 | Salai | ................... | A61B 17/2841 294/99.2 |
| 5,121,624 | A * | 6/1992 | Haughian | ................. | B25B 7/06 16/422 |
| 5,441,515 | A * | 8/1995 | Khosravi | ................... | A61F 2/93 606/194 |
| 5,573,530 | A * | 11/1996 | Fleury | ................. | A61B 17/221 606/1 |
| 5,795,242 | A * | 8/1998 | Ree | ........................ | A63B 60/14 473/303 |
| 6,121,143 | A * | 9/2000 | Messner | ................. | B24B 37/04 438/692 |
| 6,361,317 | B1 * | 3/2002 | Rahman | ................... | A61C 3/00 433/141 |
| 6,596,000 | B2 * | 7/2003 | Chan | ..................... | A61B 17/30 606/107 |
| 7,588,523 | B2 * | 9/2009 | Horner | ................... | B29C 65/10 15/230.11 |
| 8,418,321 | B1 * | 4/2013 | Heiman | ................... | B25G 1/06 15/143.1 |
| 8,424,164 | B2 * | 4/2013 | Gill | ....................... | B25G 1/102 16/421 |
| 8,573,981 | B2 * | 11/2013 | Morag | ................... | A43B 5/025 434/251 |
| 8,608,774 | B1 * | 12/2013 | Alshemari | ............ | A61B 17/30 606/210 |
| 8,657,851 | B2 * | 2/2014 | Aufaure | ................. | A61B 17/30 433/4 |
| 9,370,876 | B2 * | 6/2016 | Rule | ....................... | B24D 3/20 |
| 9,878,102 | B2 * | 1/2018 | Julian | .................... | A61M 5/20 |
| 9,913,630 | B2 * | 3/2018 | Mugan | ................ | A61B 10/0283 |
| 2002/0142857 | A1 * | 10/2002 | Huang | ................... | A63B 53/14 473/300 |
| 2004/0109980 | A1 * | 6/2004 | Chen | ..................... | A63B 49/08 428/131 |
| 2004/0121850 | A1 * | 6/2004 | Rohrer | ................... | A63B 53/14 473/300 |
| 2007/0082750 | A1 * | 4/2007 | Rose | ...................... | A63B 53/14 473/300 |
| 2007/0100201 | A1 * | 5/2007 | Komiya | ............. | A61B 1/00133 600/106 |
| 2009/0259201 | A1 * | 10/2009 | Hwang | ................... | A61B 5/153 604/263 |
| 2009/0326671 | A1 * | 12/2009 | Schofield | ........... | A61B 17/1659 623/23.5 |
| 2010/0132530 | A1 | 6/2010 | Chen | | |
| 2010/0162528 | A1 * | 7/2010 | Chen | ....................... | B25G 1/10 16/422 |
| 2010/0229693 | A1 * | 9/2010 | Chen | .................. | B23B 31/1071 81/60 |
| 2010/0298865 | A1 * | 11/2010 | Aufaure | .................. | A61B 17/30 606/210 |
| 2010/0324577 | A1 * | 12/2010 | Dunn | .................. | A61B 17/3213 606/167 |
| 2011/0048177 | A1 * | 3/2011 | Lin | ........................ | B25B 13/04 81/58 |
| 2011/0079118 | A1 * | 4/2011 | Lee | ........................ | B25B 23/16 81/177.7 |
| 2012/0042478 | A1 * | 2/2012 | Bridges | .................... | B25G 1/10 16/430 |
| 2012/0116361 | A1 * | 5/2012 | Hanlon | ................... | A61F 9/007 606/1 |
| 2012/0137472 | A1 | 6/2012 | Gill | | |
| 2012/0168107 | A1 * | 7/2012 | Waeschle | ......... | A61B 17/06066 163/5 |
| 2012/0221032 | A1 * | 8/2012 | Duperier | ........... | A61B 17/3211 606/170 |
| 2012/0253364 | A1 * | 10/2012 | Perin | .................. | A61B 17/2841 606/148 |
| 2012/0265177 | A1 * | 10/2012 | Beedall | ................ | A61B 17/162 606/1 |
| 2013/0175067 | A1 * | 7/2013 | Parel | ........................ | B25F 5/02 173/170 |
| 2013/0281784 | A1 * | 10/2013 | Ray | ........................ | A61B 1/32 600/205 |
| 2013/0305886 | A1 * | 11/2013 | Gallegos | .................. | B25G 3/24 81/60 |
| 2014/0046363 | A1 * | 2/2014 | Frimand Ronnow | ....................... | A61B 17/062 606/205 |
| 2015/0305762 | A1 * | 10/2015 | Dunn | ..................... | A61B 17/30 606/205 |
| 2016/0008523 | A1 * | 1/2016 | Nino | ...................... | A61B 17/16 604/319 |
| 2016/0317214 | A1 * | 11/2016 | Kirwan, Jr. | ......... | A61B 18/1442 |
| 2016/0324562 | A1 * | 11/2016 | Baker | ................ | A61B 17/8875 |
| 2017/0251966 | A1 * | 9/2017 | Crawford | ............. | A61B 5/1422 |
| 2018/0092585 | A1 * | 4/2018 | Hwang | ................... | A61B 5/153 |

FOREIGN PATENT DOCUMENTS

| | | | | | |
|---|---|---|---|---|---|
| EP | | 2764839 A1 * | 8/2014 | ............. | A61B 17/30 |
| JP | | 2001310273 A | 11/2001 | | |
| JP | | 2012143540 A | 8/2012 | | |
| JP | | 2012517869 A | 8/2012 | | |
| WO | | 2010094603 A1 | 8/2010 | | |
| WO | | 2013/130365 | 9/2013 | | |
| WO | | 2013130365 A1 | 9/2013 | | |

OTHER PUBLICATIONS

Japanese office action for patent application No. 2016-570175 dated Oct. 2, 2018.

* cited by examiner

MEDICAL INSTRUMENT

BACKGROUND OF THE INVENTION

The present invention relates to a medical instrument, in particular a surgical instrument, with an intervention portion for a medical intervention, and with a handle designed for holding the instrument, with a handle surface portion which has an arrangement with shapings and, formed between the shapings, enclosure portions.

Numerous medical instruments are known from the prior art. Along a longitudinal axis of the medical instrument, an intervention portion for a medical, in particular surgical or microsurgical, intervention is arranged at a distal end (remote from the surgeon) of the medical instrument, also known as the instrument tip, and a handle is arranged at a proximal end of the medical instrument.

On account of hygiene regulations, these instruments are usually produced entirely from stainless metal, generally chrome vanadium, stainless steel or titanium, which has a smooth surface structure without introduced depressions or elevations.

In order that the surgeon can handle the medical instrument and in particular the intervention portion readily for the medical intervention without the surgeon's hand or finger, manipulating the medical instrument, slipping off the medical instrument, the medical instruments are provided with a handle having a handle surface portion.

In a first type of medical instruments configured in a generic manner, the handle surface portion has, as shapings, elongate grooves milled into a surface of the handle, between which the remaining material, which has not been milled away, of the surface of the handle forms raised elongate ribs as enclosure portions. In this case, the deep grooves frequently each have a pyramid shape with a triangular cross-sectional profile, such that a right angle is defined between the cross-sectional profiles of adjacent grooves. These grooves and ribs can prevent the hand, and in particular the force-applying thumb, of the surgeon from slipping off particularly effectively when they are arranged such that their respective longitudinal directions define an angle of 60 degrees with the longitudinal axis of the medical instrument. Then, the grooves and ribs are oriented perpendicularly to a longitudinal axis of the thumb to be applied to the handle, the longitudinal axis of which thumb defines an angle of 30 degrees with the longitudinal axis of the instrument in conventional medical instruments.

In a second type of medical instruments configured in a generic manner, the handle surface portion has, as shapings, a first group of mutually parallel elongate grooves and a second group of mutually parallel elongate grooves in the surface of the handle, wherein the grooves of the first group define a right angle with the grooves of the second group. The remaining material, which has not been milled away, of the surface of the handle, which material is bounded by the grooves of the two groups, forms a structure of raised rectangular lands.

Particularly high demands are imposed on medical and in particular surgical instruments with regard to their cleaning properties and grip. As far as the aspect of grip is concerned, an aggravating factor is that the surgeon and user of the medical instrument wears gloves, usually made of latex, for hygiene reasons for personal protection and for protecting the patient. Therefore, the handle of the medical instrument has to be configured such that the handle surface portion in contact with the glove enclosing the surgeon's hand allows the application of a high frictional force without the glove slipping on the handle surface portion and without a finger accommodated in the glove slipping, said finger exerting a force on the handle surface portion. Although the handle surface portion has to be configured for the application of high static friction and, in the case of incipient slipping, to apply high sliding friction, the handle surface portion has to be designed such that it does not damage the surgeon's glove for example by sharp-edged transitions between the ribs and grooves. Furthermore, the handle surface portion has to be configured such that the glove does not stick to the handle surface portion or get stuck in the grooves in the handle surface portion when the surgeon's fingers come away from the medical instrument.

As far as the cleaning properties are concerned, in the case of medical instruments, importance is attached to the fact that contaminants, for example dried-on blood, adhering to the instrument, in particular to the handle surface portion that is provided with grooves or other depressions to achieve good grip and is thus particularly critical as far as cleaning properties are concerned, can be removed effortlessly. Since medical instruments, after rough cleaning, are subsequently steam-sterilized in an autoclave, the medical instrument should be designed such that, after steam-sterilization has taken place, no residual quantities of liquid collect in or on the instrument.

The generic medical instruments known from the prior art represent a compromise between the achievement of good grip of the instrument and good cleaning properties of the instrument.

In the case of the abovementioned first type of medical instruments configured in a generic manner, grip suffers when the force along the surface of the handle surface portion is not applied in a direction perpendicular to the grooves and ribs arranged parallel to one another, however. In this case, safe guiding of the medical instrument by the surgeon is jeopardized, since the surgeon's fingers applied to the grooves and ribs can slip in the direction of the respective longitudinal directions of the grooves and ribs. In the event of such slipping, there is also the risk that the ribs will have a knife-blade-like action and the glove will be damaged by the movement, brought about by slipping, in the longitudinal direction of the ribs. In addition, the deep grooves that meet one another at right angles are difficult to clean.

In the case of the abovementioned second type of medical instruments configured in a generic manner, the cleaning properties suffer especially from the fact that the rectangularly formed lands are completely surrounded by grooves which form a mesh-like pattern of groove portions that intersect at right angles and are thus difficult to clean. In addition, if the raised lands are at too narrow a spacing from one another, there is a risk of the glove getting stuck between the lands.

Furthermore, in the case of both types of medical instruments configured in a generic manner, liquid accumulations in or on the grooves of the instrument can occur after steam-sterilization.

DE 10 2007 047 059 A1 describes a medical instrument having a handle surface portion which can be provided with preferably elongate depressions. Grip appears to be in need of improvement.

Prior art outside the specialist field, in which different handle concepts for non-medical implements are explained, are described in US 2012/0137472 A1, US 2013/0175067 A1 and WO 2013/130365 A1.

SUMMARY OF THE INVENTION

Therefore, it is the object of the present invention to provide a medical instrument having optimized grip, such that the medical instrument can be guided safely by the surgeon and without any risk of a hand holding the instrument from slipping on the instrument, good detachability of the glove from the handle surface portion and optimized cleaning properties compared with the prior art.

The object of the present invention is achieved by a generic medical instrument having the characterizing features disclosed herein. Additional features of further advantageous embodiments can be gathered from the disclosure and the dependent claims.

The medical, in particular surgical or microsurgical, instrument according to the invention is provided with an intervention portion for a medical intervention, and with a handle designed for holding the instrument, preferably for controlling the intervention portion, having a handle surface portion which has an arrangement with shapings and enclosure portions formed between the shapings. The intervention portion is configured to be immovable or movable, for example as forceps, or electrically activatable. According to the invention, the shapings each have a hexagonal edge with six edge portions of equal length. In this case, mutually adjoining edge portions of the edge portions of each shaping define the same angle of 120 degrees before and/or after development of the arrangement onto a flat plane. The hexagonal edge is formed by the enclosure portions, preferably of rectangular structure, formed between adjacent shapings, with the result that a honeycomb structure is obtained on the handle surface portion. In the preferred configuration with the enclosure portions of rectangular structure, three rectangular enclosure portions that are arranged at an angle to one another delimit a triangular portion.

In one embodiment, the shapings of the handle surface prtion are formed as depressions, or in other words as recesses, impressions, indentations or concavities, in the handle surface portion. The enclosure portions of the handle surface portion are raised with respect to the shapings, formed as depressions, of the handle surface portion. In this embodiment, the fingertips, or the parts, surrounding the latter, of the glove of the surgeon holding the medical instrument engage with the depressions with the respectively hexagonally formed edge, accompanied by corresponding elastic deformation of the fingertips, and rest on the enclosure portions formed in a raised manner.

Since each shaping formed as a depression has six edge portions that transition into raised enclosure portions, said edge portions being arranged on one of three axes that are offset with respect to one another through 60 degrees (or 120 degrees, respectively), the handle surface portion according to the invention of this embodiment allows very high grip of the instrument without particular consideration being given to a direction of force application by the surgeon holding the medical instrument. In addition to the very high grip and thus reduced risk of slipping, the depressions also have the effect, on account of their hexagonal edge, that the force exerted on those areas of the surgeon's gloves that are in contact with the handle surface portion is distributed evenly over a large number of contact points, and so the risk of damage to the glove is reduced compared to the known handle surface portions provided with grooves.

Since adjacent edge portions of a depression having a hexagonal edge define an obtuse and thus wide angle of 120 degrees, the depressions formed according to the invention have good cleaning properties. Furthermore, the arrangement according to the invention of the depressions prevents accumulation of residual liquid after steam-sterilization of the instrument has been carried out.

In a further embodiment, the shapings of the handle surface portion are formed as prominences, or in other words as bulges, elevations or mounds, on the handle surface portion. The enclosure portions of the handle surface portion are formed in a depressed manner with respect to the shapings, formed as prominences, of the surface handle portion. In this embodiment, the fingertips, or the areas, surrounding the latter, of the glove of the surgeon holding the medical instrument, engage with the enclosure portions which form the hexagonal edge of the shapings formed as prominences, accompanied by corresponding elastic deformation of the fingertips, and rest on the prominences, likewise accompanied by corresponding elastic deformation of the fingertips.

Since each shaping formed as a prominence has six edge portions that transition into depressed enclosure portions, said edge portions being arranged on one of three axes that are offset with respect to one another through 60 degrees (or 120 degrees, respectively), the handle surface portion according to the invention of this embodiment allows very high grip of the instrument without particular consideration being given to a direction of force application by the surgeon holding the medical instrument. In addition to the very high grip and thus reduced risk of slipping, the prominences also have the effect, on account of their hexagonal edge, that the force exerted on those areas of the surgeon's gloves that are in contact with the handle surface portion is distributed evenly over a large number of contact points, formed by the prominences and the edge portions thereof that transition into the depressed enclosure portions in the case of the handle surface portion, and so the risk of damage to the glove is reduced.

Since the enclosure portions surrounding the prominences define an obtuse and thus wide angle of 120 degrees with their respectively adjacent enclosure portion, this embodiment affords good cleaning properties and can avoid accumulation of residual liquid after steam-sterilization of the instrument has been carried out.

If the arrangement is arranged on a planar handle surface portion which has a planar surface without consideration being given to the shapings, the mutually adjoining edge portions of the edge portions of each shaping define the same angle of 120 degrees before and after the development of the arrangement onto a flat plane. Consequently, for a planar handle surface portion, no case discrimination with regard to the development is necessary and one and the same embodiment results.

If the arrangement is arranged on a curved handle surface surface portion, i.e. on a handle surface portion which, without consideration being given to the shapings, has a curved or arched surface, various embodiments are possible.

In one embodiment, the mutually adjoining edge portions of the edge portions of each shaping is define the same angle of 120 degrees before the development of the curved surface of the handle surface portion onto a flat plane. In this embodiment, the shapings are consequently arranged in the handle surface portion such that—when a single shaping is considered—the six edge portions of equal length which form the hexagonal edge of the shaping extend on the curved or arched handle surface portion of the handle in a specific flat plane for the shaping in question, such that the edge portions extend strictly in a rectilinear manner and adjacent edge portions of the shapings define the same angle of 120 degrees, and such that the edge portions are arched in a manner not corresponding to a curvature of the curved surface of the handle surface portion, and/or the adjacent edge portions of the shaping do not extend in the same level along their entire length. This goes in a corresponding manner for the other ones of the shapings, the respective six edge portions of equal length of which extend on the curved or arched handle surface portion of the handle in a specific flat plane for the shaping in question, which can differ from the specific flat plane of another shaping.

This embodiment then also allows mutually identical configurations of the shapings and thus constantly distinct properties with regard to grip and cleaning approximately over the entire handle surface portion, when the handle surface portion does not have a constant radius of curvature.

In another embodiment, the mutually adjoining edge portions of the edge portions of each shaping define the same angle of 120 degrees after the development of the curved surface of the handle surface portion onto a flat plane. In this embodiment, the shapings are consequently arranged in the handle surface portion such that—when a single shaping is considered—the six edge portions of equal length which form the hexagonal edge of the shaping extend on the curved or arched handle surface portion of the handle in a specific plane for the shaping in question, said plane representing a segment of the curved or arched surface of the handle surface portion, such that the edge portions are arched in accordance with a curvature of the arched surface of the handle surface portion, and/or the adjacent edge portions of the shaping do not extend in the same level along their entire length. This goes in a corresponding manner for the other ones of the shapings.

On account of the edge portions which are configured in an arched manner corresponding to a curvature of the arched surface of the handle surface portion, this embodiment makes it possible, for each shaping, to adapt the transition from the shaping to the enclosure portions surrounding same to the respective curvature of the arched surface of the handle surface portion. As a result, in the case of strong curvatures, sharp-edged transitions from the shaping to the enclosure portions surrounding it can be avoided.

In a further embodiment according to the invention, the shapings are arranged such that, preferably for all of the shapings, one pair of the mutually parallel ones of the edge portions of one of the shapings defines a right angle with a holding axis provided for the use of the instrument, in particular a longitudinal axis of the handle or handle surface portion and/or of the instrument. The holding axis means for example the axis along which, when the medical instrument is used as intended, the surgeon's thumb is placed on the handle surface portion.

As a result of this perpendicular arrangement, in one level of the handle surface portion, of one of the total of three pairs of parallel edge portions of each of the shapings to the holding axis, the grip provided by the handle surface portion can be optimized for a force applied in the direction of the holding axis.

In yet another embodiment according to the invention, the shapings are arranged such that an angle bisector of the mutually adjoining ones of the edge portions of the shapings extends parallel to a longitudinal axis of the handle or handle surface portion and/or of the instrument.

Then, one of the total of three pairs of parallel edge portions of each of the shapings defines a right angle with the longitudinal axis of the thumb to be applied to the handle, said longitudinal axis defining an angle of 30 degrees with the longitudinal axis of the handle or handle surface portion and/or instrument in conventional medical instruments. The grip provided by the handle surface portion can thus be optimized for a force applied in the direction of a usual holding axis for the thumb. A further advantage is that the medical instrument has invariably good grip even when rotated through 180 degrees about its longitudinal axis, since, even then, one pair of parallel edge portions of each of the shapings defines a right angle with the longitudinal axis of the thumb to be applied to the handle. This represents a considerable improvement over the abovementioned first type of medical instruments configured in a generic manner from the prior art, which lose grip when rotated through 180 degrees about the longitudinal axis, since the grooves then no longer define a right angle with the usual holding axis of 30 degrees with respect to the longitudinal axis of the instrument.

In yet another embodiment according to the invention, one of the edge portions of one of the shapings extends, preferably for all of the shapings, parallel to an adjacent one of the edge portions of another of the shapings, and an enclosure portion, arranged between these adjacent parallel edge portions, of the enclosure portions has a constant enclosure portion width measured perpendicularly to the parallel edge portions.

This results in a particularly regular honeycomb structure with uniformly high grip and equally good cleaning properties over the entire handle surface portion.

An embodiment that further develops and improves the last-described embodiment according to the invention is configured such that, in addition to the abovementioned features of the last-described embodiment according to the invention, all enclosure portions, arranged between adjacent parallel edge portions of the edge portions, of the enclosure portions have a constant, preferably identical, enclosure portion width in the range of 0.4 mm to 3.7 mm, preferably of 0.5 to 3.5, more preferably of 0.6 mm to 1.6 mm, and/or each of the shapings has, between the respectively opposite parallel edge portions thereof, a constant width, preferably identical to the other shapings, in the range of 0.7 mm to 5.7 mm, preferably 0.8 mm to 5.5 mm, more preferably of 1.0 mm to 2.4 mm.

The resulting, particularly regular honeycomb structure having the above-described dimensions provides optimal grip for medical instruments and optimal cleaning properties for medical instruments, over the entire handle surface portion.

An embodiment that yet further develops and improves the last-described embodiment according to the invention is configured such that, in addition to the abovementioned features of the last-described embodiment according to the invention, the ratio between the width of the shapings and the enclosure portion width is in the range of 1.4 to 1.8 and preferably corresponds to the golden section. A ratio corresponding to the golden section is in this case the ratio of the golden number to the number one, i.e. approximately 1.618:1. The golden number, as an irrational number, can be given only in an approximate manner. Therefore, in the context of the present invention, numbers which deviate from the mathematical definition of the golden number by less than 5 percent are deemed to be the golden number. The golden number also results from the ratio of a very high member of the Fibonacci sequence to the previous member of this sequence.

The resulting, particularly regular honeycomb structure having the above-described dimensions and ratios provides even more optimal grip for medical instruments and even more optimal cleaning properties for medical instruments, over the entire handle surface portion.

A further embodiment according to the invention is configured such that the shapings are formed, in particular consistently among one another, as a depression, in other words as recesses, impressions, indentations or concavities, or as a prominence, in other words as bulges, elevations or mounds, with respect to a level on which the hexagonal edge of the respective one of the shapings lies, and extend, in particular consistently among one another, at most in the range of 0.2 mm to 1.4 mm, preferably of 0.35 mm to 1.20 mm, perpendicularly to the level on which the hexagonal edge of the respective one of the shapings lies.

This formation of the shapings allows very good grip and good cleaning properties.

In addition to the last-described embodiment according to the invention, optionally or alternatively, at least a subset of the shapings are formed as through-holes.

This improves especially the cleaning properties of the medical instrument and prevents accumulation of residual liquids on the instrument after steam-sterilization.

A further embodiment according to the invention is configured such that the shapings are formed, in particular consistently among one another, so as to be curved. In this case, the prominences are preferably formed either as a concave depression or as a convex prominence. The radius of curvature in this case determines the degree to which accumulation of residual liquid after steam-sterilization is avoided.

This curved configuration allows an improvement in the cleaning properties and prevention of the accumulation of residual liquid on the medical instrument after steam-sterilization. Furthermore, as a result of the concave depressions or the convex prominences, light striking the medical instrument is scattered and deflected such that, compared to the known generic instruments, the dazzling effect brought about by light incident on the instrument can be reduced.

A further embodiment according to the invention is configured such that, a transition region from one of the enclosure portions to one of the shapings is formed, in particular consistently for all of the enclosure portions and all of the shapings, in an angular or rounded manner.

A transition region formed in an angular manner allows an improvement in grip, while a transition region formed in a rounded manner promotes the cleaning properties and the avoidance of the accumulation of residual liquid after steam-sterilization.

Alternatively or in addition to the last-defined embodiment according to the invention, a wall portion of one of the enclosure portions defines, in particular consistently for all of the enclosure portions and all of the shapings, a right angle or obtuse angle with a wall portion, spaced apart therefrom by the transition region, of one of the shapings.

A defined right angle allows an improvement in grip, while an obtuse angle promotes the cleaning properties and the avoidance of accumulation of residual liquid after steam-sterilization.

According to a further advantageous embodiment according to the invention, the handle surface portion is subdivided into at least two handle surface sub-portions that are spaced apart from one another at an angle of at least 20 degrees in a radial circumferential direction with respect to a longitudinal axis of the instrument, and each handle surface sub-portion is arranged over at least 10 percent of the entire radial circumferential direction in the radial circumferential direction.

As a result of the subdivision of the handle surface portion, the grip can be improved compared with a handle surface portion without subdivision, since the handle surface sub-portions can be arranged on the handle in a targeted manner for different fingers of the surgeon. On account of the more targeted and thus more efficient provision of the handle surface sub-portions rather than a single extensive handle surface portion, the cleaning properties can be improved.

A further embodiment according to the invention is configured such that the handle surface portion is subdivided into adjacent handle surface sub-portions, and one of the handle surface sub-portions has shapings formed exclusively as depressions, while the other of the handle surface sub-portions has shapings formed exclusively as prominences.

This allows combined use of the two fundamentally possible configurations of the shapings, such that a handle surface portion formed in such a way can afford all of the individual advantages of both types of shaping.

Further advantageous embodiments according to the invention result from the combination of at least two of the embodiments according to the invention that are described above or in the following text, as long as such a combination is not obviously nonsensical.

With regard to the angular dimensions and specifications of equal length mentioned in the context of this disclosure, a deviation of up to 2 degrees for the angular dimensions and of up to 2 percent with regard to the lengths are deemed to comply with said dimensions and specifications. The angular dimension of the complete circle, also known as round angle, is 360 degrees.

The instruments according to the invention, including the handle surface portion, are produced from a stainless metal, for example chrome vanadium, stainless steel or titanium. Parts of these instruments can also be manufactured from plastics materials or other materials, however.

In a preferred embodiment, the medical instrument according to the invention is neurosurgical forceps which are provided with the handle surface portion having the hexagonal structure according to the invention. As a result, good adherence of the surgeon's hand to the handle surface portion can be ensured even in the case of this particularly delicate instrument.

BRIEF DESCRIPTION OF THE DRAWINGS

Exemplary embodiments of the invention are explained in the following text with reference to the accompanying figures, in which.

DETAILED DESCRIPTION

Figure 1:
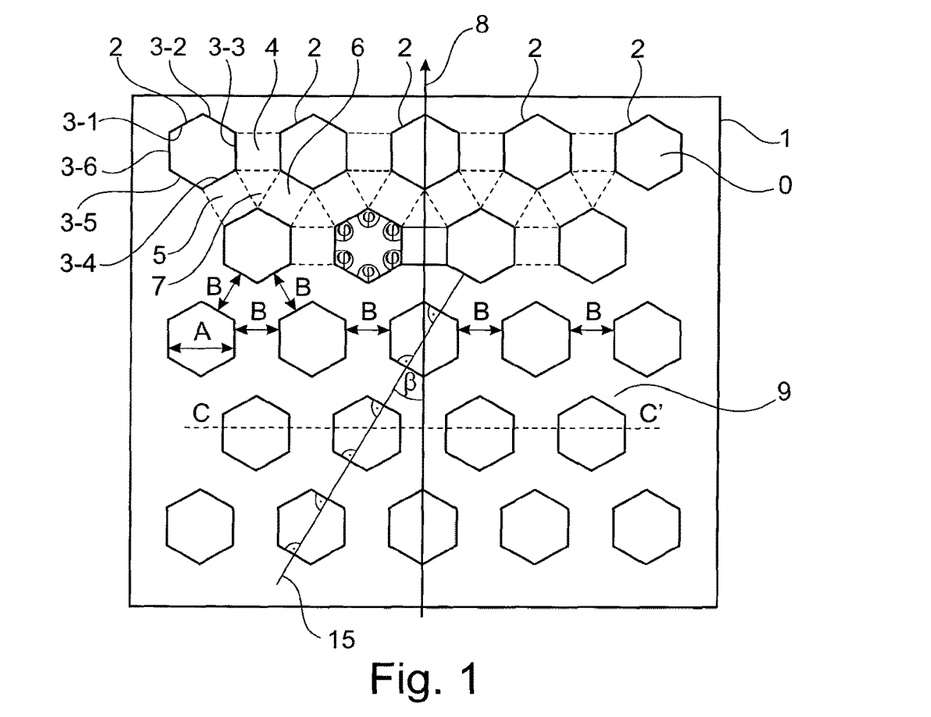
FIG. 1 shows a plan view of an arrangement according to the invention having shapings and enclosure portions formed between the shapings.

FIG. 1 shows a plan view of an arrangement according to the invention having shapings and enclosure portions formed between the shapings. The handle surface portion 1 comprises a plurality of shapings 0 with in each case one hexagonal edge 2 with six edge portions 3-1, 3-2, 3-3, 3-4, 3-5 and 3-6 of equal length, wherein mutually adjoining ones of these edge portions of one of the shapings 0 define the same angle φ=120 degrees. Formed between adjacent edge portions, extending parallel to one another, of adjacent shapings, are rectangular enclosure portions 4, 5 and 6 having sides that are oriented differently from one another. In each case one side of these three rectangular enclosure portions 4, 5 and 6 delimits a triangular enclosure portion 7 such that the rectangular enclosure portions 4, 5 and 6 surround the triangular enclosure portion 7 with sides that are oriented differently from one another. The shapings 0 have a mutually consistent width A which is defined in each case by the spacing of the opposing edge portions, for example 3-1 and 3-4, and 3-2 and 3-5, and 3-3 and 3-6, respectively, of a respective shaping 0. Adjacent parallel edge portions of adjacent shapings are spaced apart from one another consistently with the enclosure portion width B. The handle surface portion shown in FIG. 1 has a regular honeycomb structure 9. Furthermore, an angle bisector of the mutually adjoining edge portions, for example 3-1 and 3-2, and 3-4 and 3-5, respectively, of a shaping 0 is parallel to a longitudinal axis of the instrument 8, the arrow tip, marked in FIG. 1, of which points in the direction of the instrument tip. Furthermore, the holding axis 15, provided for use of the instrument, is indicated in FIG. 1, on the assumption of the abovementioned, frequently encountered holding angle β=30 degrees. The edge portions 3-1 and 3-5 of each of the shapings 0 extends perpendicularly to the holding axis 15.

The handle surface portion 1 shown in FIG. 1 comprises only shapings having a completely closed and hexagonal edge. In another embodiment, the handle surface portion can be delimited at its edges by shapings which do not have a completely closed hexagonal edge but only an open edge with fewer than six edge portions, for example with three edge portions.

Figure 2A:
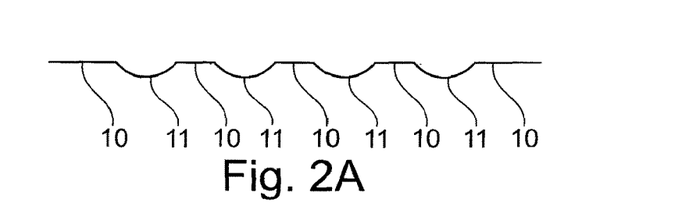
FIG. 2A shows a cross-sectional view along a section line C-C', illustrated in FIG. 1, for an embodiment in which the shapings are formed consistently as concave depressions.

FIG. 2A shows a cross-sectional view along a section line C-C', illustrated in FIG. 1, for an embodiment in which the shapings are formed consistently as concave depressions. The shapings 0 are formed as concave depressions 11, and the enclosure portions 4, 5 and 6 are formed as raised enclosure portions 10.

Figure 2B:
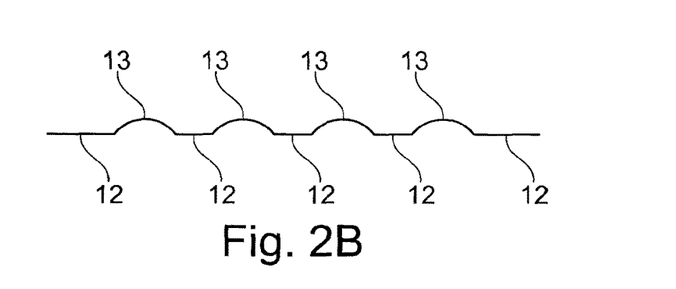
FIG. 2B shows a cross-sectional view along the section line C-C', illustrated in FIG. 1, for another embodiment, in which the shapings are formed consistently as convex prominences.

FIG. 2B shows a cross-sectional view along the section line C-C', illustrated in FIG. 1, for another embodiment, in which the shapings are formed consistently as convex prominences. The shapings 0 are formed as convex prominences 13, and the enclosure portions 4, 5 and 6 are formed as depressed enclosure portions 12.

In both of the embodiments in FIG. 2A and FIG. 2B, the shapings are formed consistently with one another with regard to the curve direction, the radius of curvature of the curves and the maximum depth of the curves.

Figure 3A:
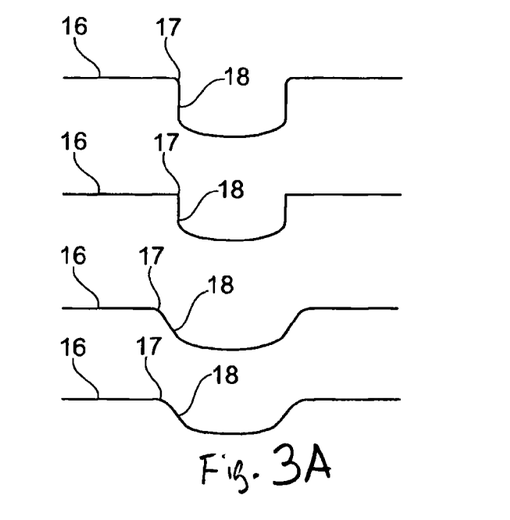
FIGS. 3A and 3B show different embodiments with regard to the transition region from one of the enclosure portions to one of the shapings and with regard to the angle defined between a wall portion of one of the enclosure portions and a wall portion, spaced apart therefrom by the transition region, of one of the shapings.
Figure 3B:
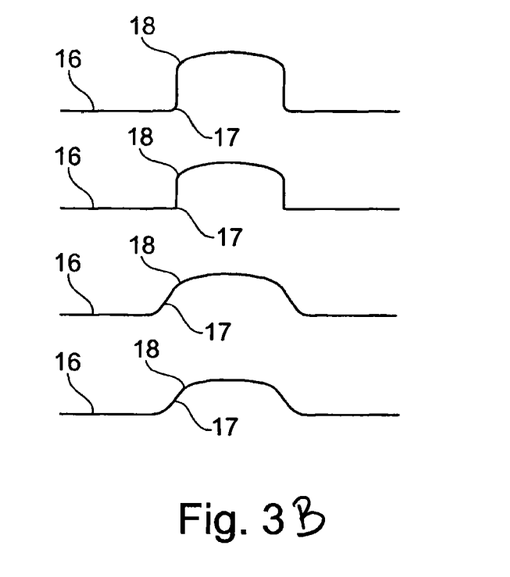

The following embodiments of possible shapings are shown from top to bottom in FIGS. 3A and 3B: a shaping formed as a depression (FIG. 3A) which has a rounded transition region 17 between the raised enclosure portion 16 and the depression 18, wherein the wall portions connected to the rounded transition region define a right angle; a shaping configured as a depression which has an angular transition region between the raised enclosure portion and the depression, wherein the wall portions connected to the angular transition region define a right angle; and a shaping formed as a depression which has a rounded transition region between the raised enclosure portion and the depression, wherein the wall portions connected to the rounded transition region define an obtuse angle; a shaping formed as a depression which has an angular transition region between the raised enclosure portion and the depression, wherein the wall portions connected to the angular transition region define an obtuse angle; a shaping formed as a prominence (FIG. 3B) which has a rounded transition region 17 between the depressed enclosure portion 16 and the prominence 18, wherein the wall portions connected to the rounded transition region define a right angle; a shaping formed as a prominence which has an angular transition region between the depressed enclosure portion and the prominence, wherein the wall portions connected to the angular transition region define a right angle; a shaping formed as a prominence which has a rounded transition region between the depressed enclosure portion and the prominence, wherein the wall portions connected to the rounded transition region define an obtuse angle; and a shaping formed as a prominence which has an angular transition region between the depressed enclosure portion and the prominence, wherein the wall portions connected to the angular transition region define an obtuse angle.

Figure 4:
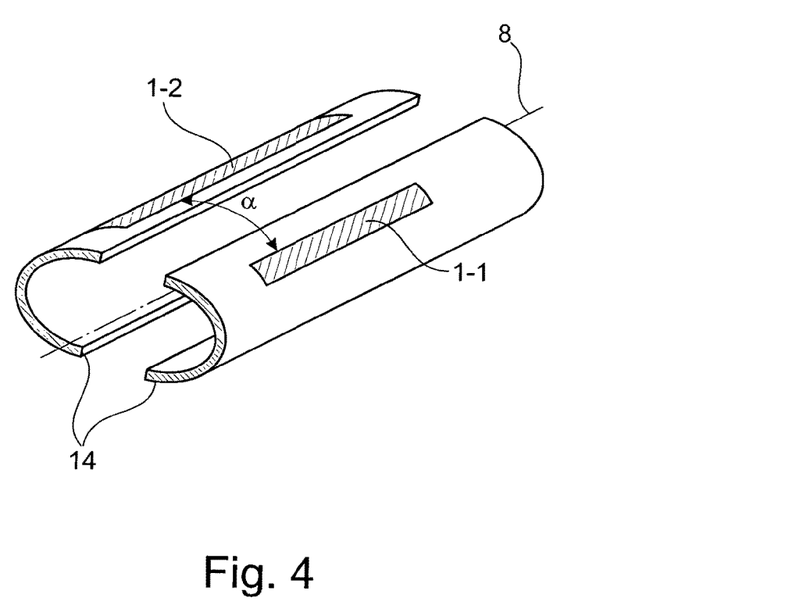
FIG. 4 shows a handle of a medical instrument having two handle surface sub-portions.

FIG. 4 illustrates a handle of a medical instrument having two handle surface sub-portions. The handle 14, extending in the direction of the longitudinal axis of the instrument 8, has two handle surface sub-portions 1-1 and 1-2 that are spaced apart from one another at an angle α in a radial circumferential direction with respect to the longitudinal axis of the instrument 8, wherein each of the handle surface sub-portions 1-1 and 1-2 is arranged over at least 10 percent of the total radial circumferential direction in the radial circumferential direction.

Figure 5A:
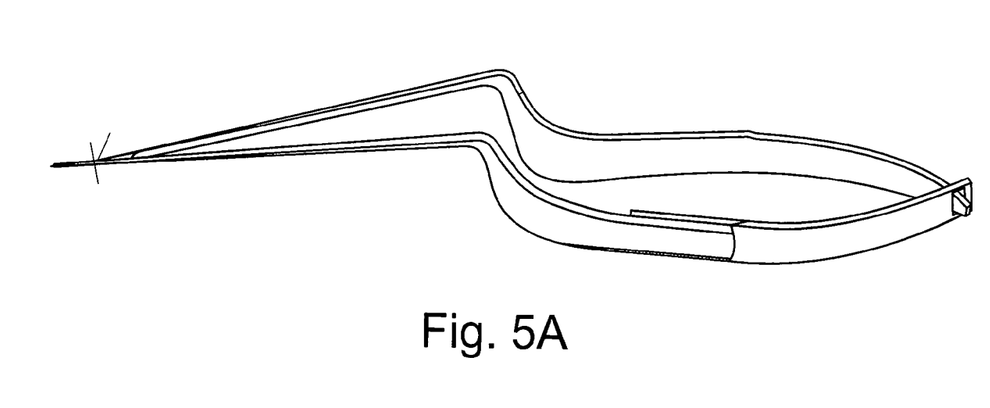
FIG. 5A shows a perspective view of an example of an instrument according to the invention.
Figure 5B:
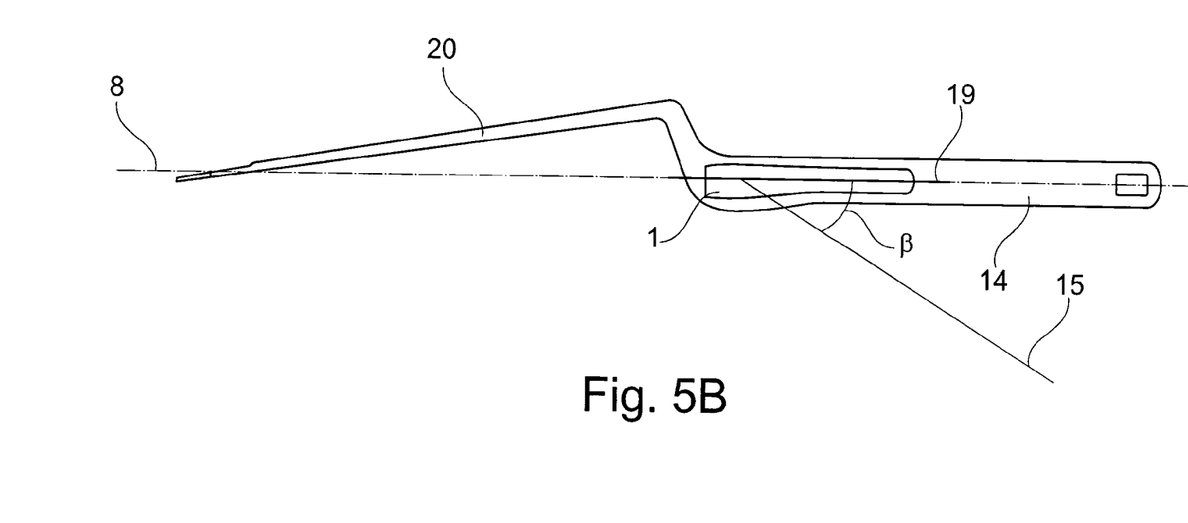
FIG. 5B shows a side view of the example of an instrument according to the invention from FIG. 5A.

FIG. 5A and FIG. 5B show an example of a medical instrument according to the invention. The medical instrument according to the invention has an intervention portion 20 and a handle 19 having a handle surface portion 1. A longitudinal axis of the instrument 8 extends in the same direction as a longitudinal axis of the handle 19. The longitudinal axis of the handle 19 and a holding axis 15, provided for use of the instrument, for the thumb define an angle β.

The embodiments according to the invention that are explained by way of example do not restrict the scope of protection of the invention. The scope of protection of the invention is defined by the appended claims.

The invention claimed is:

1. A medical instrument, in particular a surgical instrument, with an intervention portion (20) for a medical intervention, and with a grip (14) designed for holding the instrument, with a grip surface portion (1) which is made of a stainless metal and which has an arrangement with shapings (0) and, formed between the shapings, enclosure portions (4, 5, 6, 7),
wherein
the shapings (0) each have a hexagonal edge (2) with six edge portions of equal length (3-1, 3-2, 3-3, 3-4, 3-5, 3-6), wherein mutually adjoining edge portions (3-1, 3-2; 3-2, 3-3; . . . ) of each shaping (0) upstream and/or downstream of a winding of the arrangement on a plane surface span the same angle (φ) of 120 degrees, and wherein the edge (2) is formed by the enclosure portions (4, 5, 6, 7) formed between adjacent shapings (0), as a result of which a honeycomb structure (9) is obtained.

2. The instrument according to claim 1, wherein the shapings (0) are arranged so that a pair of the edge portions (3-2, 3-5), parallel to one another, of one of the shapings spans a right angle with a holding axis (15) provided for the use of the instrument.

3. The instrument according to claim 2, wherein the holding axis (15) is a longitudinal axis of the grip and/or of the instrument (19, 8).

4. The instrument according to claim 1, wherein the shapings are arranged so that an angle bisector of the mutually adjoining edge portions (3-1, 3-2; 3-4, 3-5) of the shapings extends parallel to a longitudinal axis of the grip and/or of the instrument (19, 8).

5. The instrument according to claim 1, wherein one of the edge portions of one of the shapings runs parallel to an adjacent one of the edge portions of another of the shapings, and an enclosure portion (4, 5, 6) of the enclosure portions, arranged between these adjacent parallel edge portions, has a constant enclosure portion width (B), measured perpendicularly on the parallel edge portions.

6. The instrument according to claim 5, wherein all enclosure portions (4, 5, 6) of the enclosure portions arranged between adjacent parallel edge portions have a constant, enclosure portion width (B) in the range of 0.4 mm to 3.7 mm, and/or each of the shapings between their respectively opposite parallel edge portions (3-1, 3-4; 3-2, 3-5; 3-3, 3-6) has a constant width (A) in the range of 0.7 mm to 5.7 mm.

7. The instrument according to claim 6, wherein the ratio between the width of the shapings (A) and the enclosure portion width (B) lies in the range of 1.4 mm to 1.8 mm and preferably corresponds to the golden ratio.

8. The instrument according to claim 6, wherein the enclosure portion width (B) is in the range of 0.5 mm to 3.5 mm.

9. The instrument according to claim 6, wherein the enclosure portion width (B) is in the range of 0.6 mm to 1.6 mm.

10. The instrument according to claim 6, wherein the constant width (A) is in the range of 0.8 mm to 5.5 mm.

11. The instrument according to claim 6, wherein the constant width (A) is in the range of 1.0 mm to 2.4 mm.

12. The instrument according to claim 6, wherein the constant width (a) is in the range of preferably 0.8 mm to 5.5 mm.

13. The instrument according to claim 1, wherein the shapings (0) are constructed as a depression (11) or as a bulge (13) with respect to a plane on which the hexagonal edge (2) of the respective one of the shapings lies, and extend as a maximum in the range of 0.2 mm to 1.4 mm perpendicularly to the plane on which the hexagonal edge (2) of the respective one of the shapings lies, and/or at least a subset of the shapings (0) is constructed as through-holes.

14. The instrument according to claim 13, wherein the maximum is in the range of 0.35 mm to 1.20 mm.

15. The instrument according to claim 1, wherein the shapings are constructed so as to be curved as a concave depression (11) or as a convex bulge (13).

16. The instrument according to claim 1, wherein a transition region (17) from one of the enclosure portions to one of the shapings is constructed in an angular or rounded manner, and/or wherein, a wall portion (16) of one of the enclosure portions spans a right angle or obtuse angle with a wall portion (18) of one of the shapings spaced apart thereto by the transition region.

17. The instrument according to claim 1, wherein the grip surface portion is divided into at least two partial grip surface portions (1-1, 1-2) spaced apart from one another in an angle ($\alpha$) of at least 20 degrees in a radial circumferential direction to a longitudinal axis of the instrument (8), and wherein each partial grip surface portion is arranged in the radial circumferential direction on at least 10 percent of the entire radial circumferential direction.

18. The instrument according to claim 1, wherein the grip surface portion (1) is divided into adjacent partial grip surface portions, and one of the partial grip surface portions has shapings (0) configured exclusively as depressions (11), whilst the other of the partial grip surface portions has shapings (0) configured exclusively as bulges (13).

19. The instrument according to claim 1, wherein the grip (14) is designed for actuating the intervention portion.

* * * * *